United States Patent [19]

Cipullo

[11] Patent Number: 5,414,152
[45] Date of Patent: May 9, 1995

[54] METHOD FOR EXTENDING THE ACTIVITY OF ACIDIC ION EXCHANGE CATALYSTS

[75] Inventor: Michael J. Cipullo, Prattville, Ala.

[73] Assignee: General Electric Company, Pittsfield, Mass.

[21] Appl. No.: 241,236

[22] Filed: May 10, 1994

[51] Int. Cl.$^6$ .................. C07C 37/20; C07C 39/16
[52] U.S. Cl. ........................ 568/727; 568/722; 568/723; 568/724; 568/728
[58] Field of Search .............. 568/727, 728, 722, 723, 568/724

[56] References Cited

U.S. PATENT DOCUMENTS

| | | | |
|---|---|---|---|
| 2,858,342 | 10/1958 | Bender et al. | 568/727 |
| 3,634,341 | 1/1972 | Gammill et al. | 568/727 |
| 3,760,006 | 9/1973 | Gammill et al. | 568/727 |
| 4,045,379 | 8/1977 | Kwantes et al. | 260/727 |
| 4,107,218 | 8/1978 | Miller | 568/724 |
| 4,294,995 | 10/1981 | Faler et al. | 568/728 |
| 4,346,247 | 8/1982 | Faler et al. | 568/728 |
| 4,396,728 | 8/1983 | Faler | 521/32 |
| 4,400,555 | 8/1983 | Mendiratta | 568/728 |
| 4,584,416 | 4/1986 | Pressman et al. | 568/727 |
| 5,075,511 | 12/1991 | Li | 568/727 |
| 5,105,027 | 4/1992 | Desmurs et al. | 568/727 |

Primary Examiner—Werren B. Lone

[57] ABSTRACT

The addition of 3-mercaptopropionic acid or the organic ester thereof to the reaction mixture slows the rate of deactivation of cationic catalyst resins containing mercaptan promoter sites, during preparation of bisphenols by the condensation of a ketone with a phenol.

11 Claims, 4 Drawing Sheets

METHOD FOR EXTENDING THE ACTIVITY OF ACIDIC ION EXCHANGE CATALYSTS

BACKGROUND OF THE INVENTION

1. Field of the Invention

The invention relates to catalysts and more particularly to acidic cation exchange resins used as catalysts to promote condensations of ketones with phenol compounds.

2. Brief Description of the Prior Art

Acidic cation exchange resins have been employed to catalyze the condensation of ketones with phenols for a number of years; see for example the early description found in U.S. Pat. No. 3,242,219. In more recent years, improvements to the catalyst have included chemical modification. The modifications generally involve covalent or ionic attachment of an organic mercaptan species ("promoter") to the resin which provides enhanced reaction activity or selectivity relative to the unmodified resin. For example, the U.S. Pat. No. 4,294,995 (incorporated herein by reference thereto) describes a sulfonated polystyrene ion-exchange resin having organo mercaptan promoter groups attached to the backbone sulfone radicals by covalent nitrogen-sulfur linkages. Representative of other resins modified in this manner are those described in U.S. Pat. 3,394,089; 3,634,341; 4,294,995; 4,346,247; 4,400,555; 4,424,283; 4,584,416; 5,075,511; all of which are incorporated herein by reference thereto.

Unfortunately, the catalytic activity and selectivity of the cation exchange catalysts modified to attach a mercaptan promoter is often lost after varying periods of use. Deactivation can occur in as short a time as 2 to 6 weeks depending on several factors, including promoter type and flow rates (production rates) through the resin. This is a particular problem, when the catalyst is employed in the commercial preparation of bisphenol-A by the condensation of acetone with phenol. The active sites of the catalyst may become blocked with organic tars incident to the condensation or chemically modified. The resin must be replaced or regenerated causing significant expense, process complication, and downtime. Regeneration, when possible, often involves treatment with an aqueous strong acid to remove the promoter and tarry by-products.(see for example the method of U.S. Pat. No. 4,051,079), followed by reattachment of fresh promoter.

The ideal solution to solving the problem of catalyst deactivation is to delay or prevent blocking of the promoter site. We have now found a method of preventing or reducing the rate of deactivation without interrupting the use of the catalyst in processes for the condensation reactions it is employed to catalyze.

Advantages of the method of the invention include the elimination of catalyst regeneration and extension of time periods between catalyst regenerations (a large capital investment). Studies reveal the product selectivity is not adversely affected by the method of the invention.

SUMMARY OF THE INVENTION

The invention comprises, in a process for the reaction of a ketone with a phenol, in the presence of an acidic cation exchange resin having organomercaptan promoter groups, the improvement which comprises; adding to the reaction mixture from about 100 to about 5000 ppm of 3-mercapto-propionic acid or the organic ester thereof.

The amount of 3-mercaptopropionic acid or ester added is preferably within the range of from about 1000 to 4000 PPM of the reaction mixture.

BRIEF DESCRIPTION OF THE DRAWINGS EMBODIMENTS OF THE INVENTION

DETAILED DESCRIPTION OF THE PREFERRED EMBODIMENT OF THE INVENTION

Figure 1:
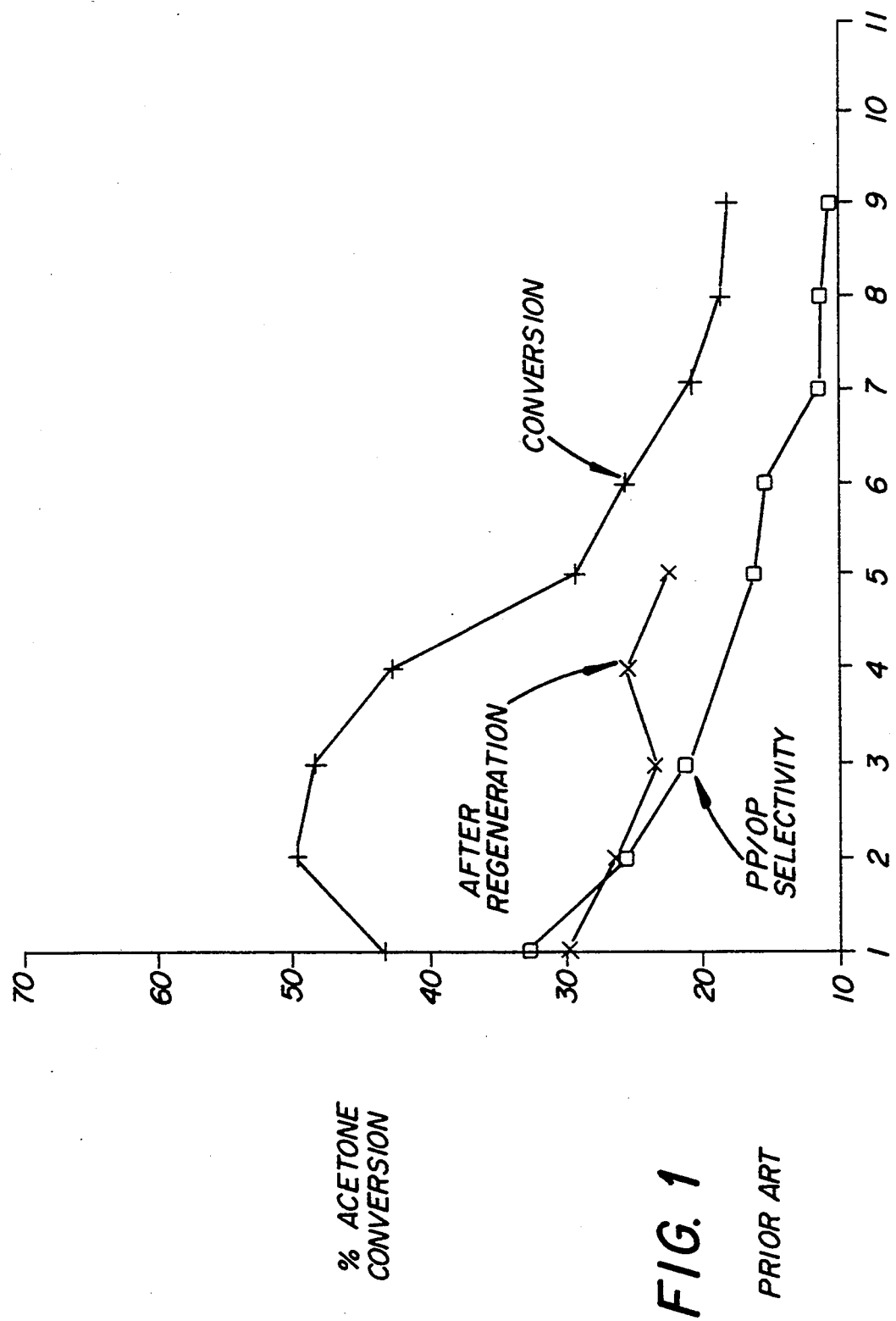
FIG. 1 is a graphical representation showing catalyst life before practice of the invention (prior art).

Processes for the synthesis of bisphenols by the condensation of a ketone with a stoichiometric excess of a phenol compound, are generally well known; see for example the descriptions given in the U.S. Pat. No. 3,634,341; 3,760,006; 4,045,379; 4,107,218; 4,294,995; 4,346,247; 4,396,728; 4,400,555; 4,424,283; 4,584,416; and 5,075,511, all of which are incorporated herein by reference thereto. The processes may be carried out continuously or in batch procedures.

In general, the processes may be carried out by bringing the ketone and a stoichiometric excess of the phenol together in a reaction zone, at a temperature of from about 40° C. to 95° C. in the presence of a cationic exchange resin under ambient atmospheric conditions. In some processes, higher than atmospheric pressures may be employed, generally within the range of 1–10 atmospheres. The bisphenol product can then be separated from the reaction mixture by conventional procedures well known in the art, including by distillation, crystallization and like methods.

In the commercial process described above the cationic exchange resin catalyst generally employed is a sulfonated aromatic resin, modified to have mercaptan groups covalently or ionically bound to the resin as promoter sites. Representative of such cationic exchange resins are those described in the U.S. Pat. No. 3,760,006; 3,634,341; 4,045,379; 4,294,995; 4,346,247; and 4,820,740, all of which are incorporated herein by reference thereto.

In general, the resins employed are chemically modified sulfonated aromatic resins. The polymers are hydrocarbon polymers having a plurality of pendant sulfonic acid groups. Examples include sulfonated polystyrene or poly(styrenedivinyl-benzene) copolymer and sulfonated phenolformaldehyde resins. The sulfonated resins are commercially available in water swollen form as micro-recticular and macro-recticular types. Specific examples of suitable resins are Amberlite IR-120H, Amberlyst 15H, Amberlyst 31, Dowex 50-X-4, Dowex MSC-1H, Duolite C-26, Permutit QH, Chempro C-2 and Imac C8P/H (Amberlite, Amberlyst, Dowex, Duolite, Permutit, Chempro and Imac are registered U.S. Trademarks). Further examples of such ion exchangers as well as methods for preparing such ion exchangers are described in the Encyclopedia of Polymer Science and Technology, 1967, vol. 7, pages 695 to 708. The exchange capacity of the acidic resin is preferably at least 2.0 meq. H+/g of dry resin, with exchange capacities in the range of from 3.0 to 5.5 meq. H+/g (dry resin)..particularly preferred. Sulfonation may be by the process described in U.S. Pat. No. 2,366,007 which is incorporated herein by reference thereto.

The sulfonated aromatic resins are modified to include mercaptan promoter sites and contain proportions of these sites randomly interspersed with the pendant sulfonic acid groups. For example, catalysts preferably used in the improved process of the invention are sulfonated poly(styrene-divinylbenzene) copolymers having pendant groups of the formulae:

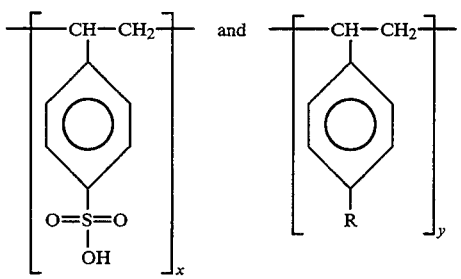

wherein x plus y equals 100% of the groups, x varies from about 60% to 99%, preferably from about 65% to about 85%, of the groups and y varies from 1% to about 40%, preferably from about 15% to about 35%, of the groups; and R is a group selected from those of the formula:

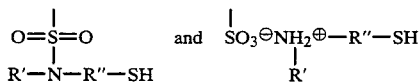

wherein R' represents hydrogen or alkyl and R" is alkylene.

The term "alkyl" as used herein means the monovalent moiety obtained upon removal of a hydrogen atom from a saturated hydrocarbon having 1-12 carbon atoms, to allow for bonding to the nitrogen atom. Representative of alkyl are methyl, ethyl, propyl, butyl, pentyl, hexyl, heptyl, octyl, nonyl, decyl, dodecyl, undecyl and isomeric forms thereof. The term "alkylene" as used herein means a saturated hydrocarbon of 1-12 carbon atoms where a total of two hydrogen atoms have been removed to allow for bonding to a nitrogen or sulfur atom. Representative of alkylene are methylene, ethylene, propylene, butylene, pentylene, hexylene, heptylene, octylene, nonylene, decylene, dodecylene, undecylene and isomeric forms thereof.

The process of the invention is advantageously carried out in the synthesis of a wide variety of bisphenols such as 1-phenyl-1,1 -bis(4-hydroxyphenyl) ethane; 1-methyl-1,1 -bis(4-hydroarylphenyl) ethane and the like. It is a preferred improvement in the synthesis of 2,2-bis-(4-hydroxyphenyl) propane (bisphenol-A).

The commercial preparation of bisphenol-A may be carried out in a number of ways. The reaction zone may comprise a single reactor or two or more reactors in series or in parallel. In the case of a multi-reactor reaction zone, suitably all of the phenol reactant is fed to the first reactor and the acetone reactant is either fed all to the first reactor or divided between the first and second and possibly further reactors.

The molar ratio of phenol to acetone is at least 2 to 1 with a stoichiometric excess of phenol being preferred. Molar ratios are preferably from 3:1 to 40:1, with molar ratios of from 10:1 to 30:1 being most preferred. The optimum ratio depends on reaction conditions, e.g., temperature of reaction and desired conversion.

The reaction temperature in the reactor zone may vary from 40° C. to 95° C. with reaction temperatures in the range of from 55° C. to 90° C. being preferred.

The reaction time in the reactor zone may also vary and depends on reaction temperature and the type of reactor. For example, in a continuous feed, tubular reactor, the liquid hour space velocity (LHSV) of the feed may vary between wide limits with velocities in the range of from 0.2 to 40 liters feedstream/liter catalyst$^{-1}$/hour$^{-1}$.

The improved process of the present invention is carried out by admixture with the reactants for the condensation reaction, minor proportions of 3-mercaptopropionic acid or the organic ester thereof, preferably the alkyl ester. The term "alkyl" is as defined above. The 3-mercaptopropionic acid is a well known compound readily available in the commercial market. The alkyl esters thereof are prepared by esterification of the acid with appropriate alcohols such as methyl, ethyl, propyl, butyl, heptyl, hexyl, octyl, nonyl, decyl, dodecyl and undecyl alcohols. The method of preparation is described for example in Baker et al., J. Org. Chem. 12, 171 (1947).

The following examples describe the manner and process of making and using the invention and set forth the best mode contemplated by the inventors for carrying out the invention, but should not be construed as limiting.

A tubular reactor with a feed inlet and a product outlet was maintained at a temperature of about 70° C. The reactor was charged with one of two catalysts and fed a reaction mixture of phenol and acetone (6% by weight acetone in pure phenol). At a weighted hour space velocity of 12.0 grams of feed per gram of dry catalyst per hour. the product bisphenol-A was collected over a period of time, with periodic analysis to determine the percentage of conversion and selectivity (p,p'/o,p' effected by the catalyst.

EXAMPLE 1

This example is not an example of the invention but is made for comparative purposes.

The reactor was charged with a sulfonated polystyrene polymer catalyst prepared in accordance with the procedure described in Example 1 of the U.S. Pat. No. 4,396,728 and having approximately 80% pendant sulfonyl styryl groups and 20% of chemically combined N-propylaminopropylmercaptan groups of formula:

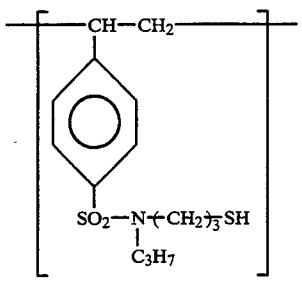

The reactor was run for a period of 9 days with periodic analysis for the product bisphenol-A to determine the percentage of acetone conversion and selectivity of the catalyst to direct the synthesis to the p,p' isomer. The conversion is plotted in the graph shown in the accompanying drawing of FIG. 1 by the symbol "+" and shows rate of deactivation (55% conversion to 20% conversion over 9 days with loss in selectivity (pp/op'=30 to 10), shown by the symbol "□".

After the initial deactivation, an attempt was made to regenerate the spent catalyst while still in the reactor. First the catalyst was washed with 1 l of 80/20 phenol/water (v/v). Next, an 80/20 phenol/water (v,v) solution containing 4% citric acid was recirculated for 20 hours through the catalyst. A p-toluene sulfonic acid wash followed, then a water wash was performed until neutral. The reactor was then started up directly with phenol/acetone reactants. As shown in FIG. 1 by the symbol "x" the "regenerated" resins's activity increased, but did not reach the initial activity observed when it was first started up.

EXAMPLE 2

Figure 2:
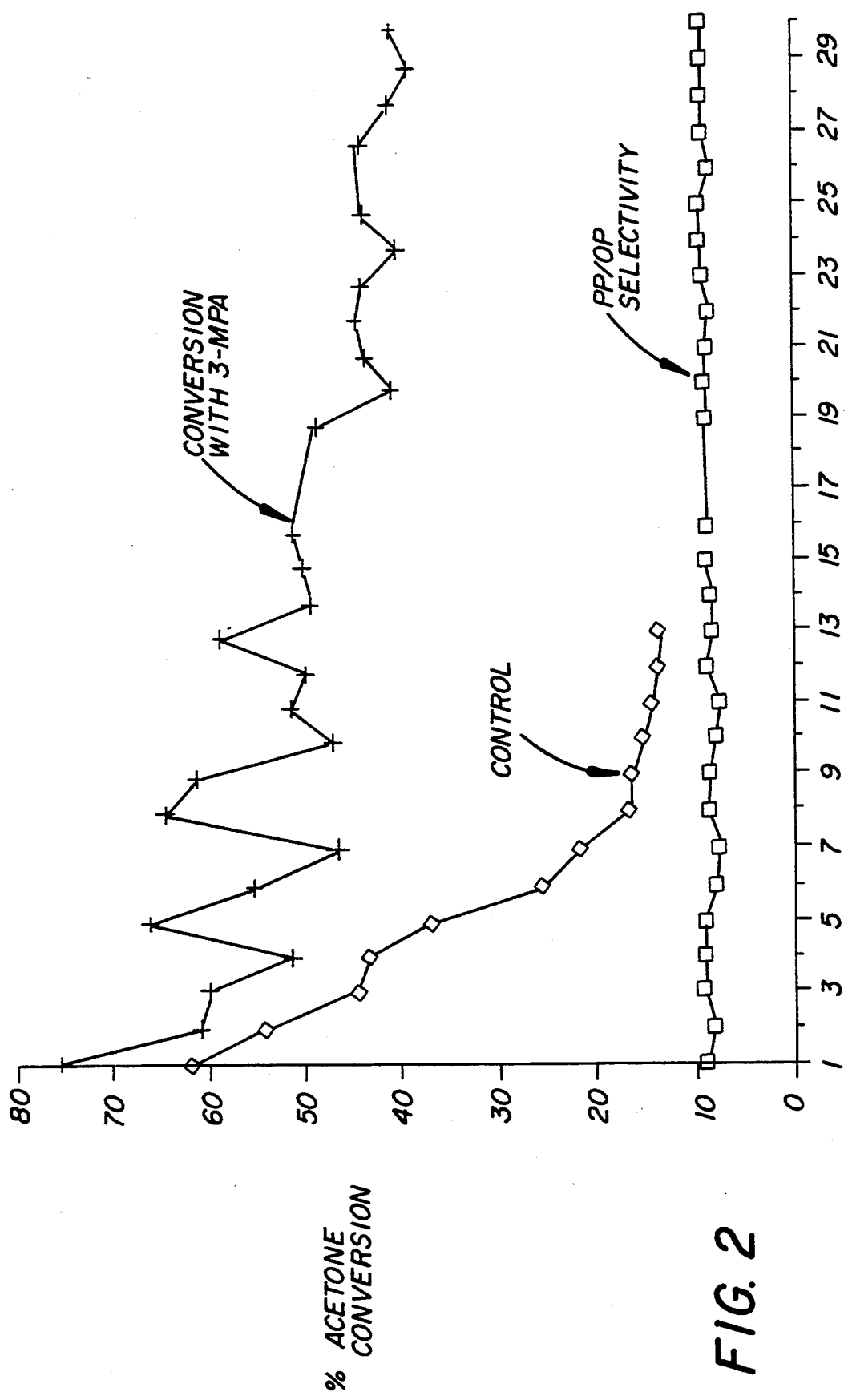
FIG. 2 is a graphical representation showing catalyst life extended by the practice of the present invention when the catalyst is a sulfonated polystyrene having mercaptan promotor groups covalently bound to the resin.

The procedure of Example 1, supra., was repeated, except that 3800 PPM of 3-mercaptanpropionic acid was added to the feed reaction mixture. The feed also included recycle by-products and p,p-bisphenol-A. The reaction was run for 30 days. The product analysis over this period is plotted in FIG. 2 of the accompanying drawings and shows (symbol "+") higher initial activity and reduced rate of deactivation (~65% conversion to 40% conversion over 20+ days) compared to a base-line control (symbol " ") run without the additive above. Acetone conversion appeared to level off around 35 to 40% when the reactor was stopped after 30 days.

Selectivity also decreased during the deactivation period, (symbol "□") then leveled off. Outlet pp/op' dropped from 9 to 6.3 while pp/op' ratio of material formed fell from 14/1 to 6.3/1 during the run. The apparent smaller reduction in the effluent pp/op' ratio is due to the reduced activity and high level of o,p' bisphenol-A in the reactor feed.

For comparative purposes, a reaction was run on a larger scale for 13 days with the catalyst of Example 1. The data collected has been plotted for comparison, in the graph of FIG. 2 (symbol " ").

EXAMPLE 3

The general procedure of Example 2 supra., was repeated except that the catalyst charged to the reactor was a sulfonated polystyrene resin prepared by modification of the cationic exchange resin XE-364 available from Rohm and Haas Company, Philadelphia, Pa. The resin may be modified by reaction with 2,2-dimethyl-1,3-thiazolidine following the procedure described in U.S. Pat. No. 2,858,342 or 3,634,341 to obtain a sulfonated polystyrene resin having about 80 percent sulfonyl styryl groups and about 20 percent of pendant groups of the formula:

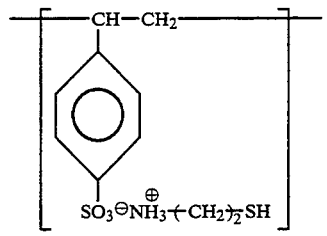

Figure 3:
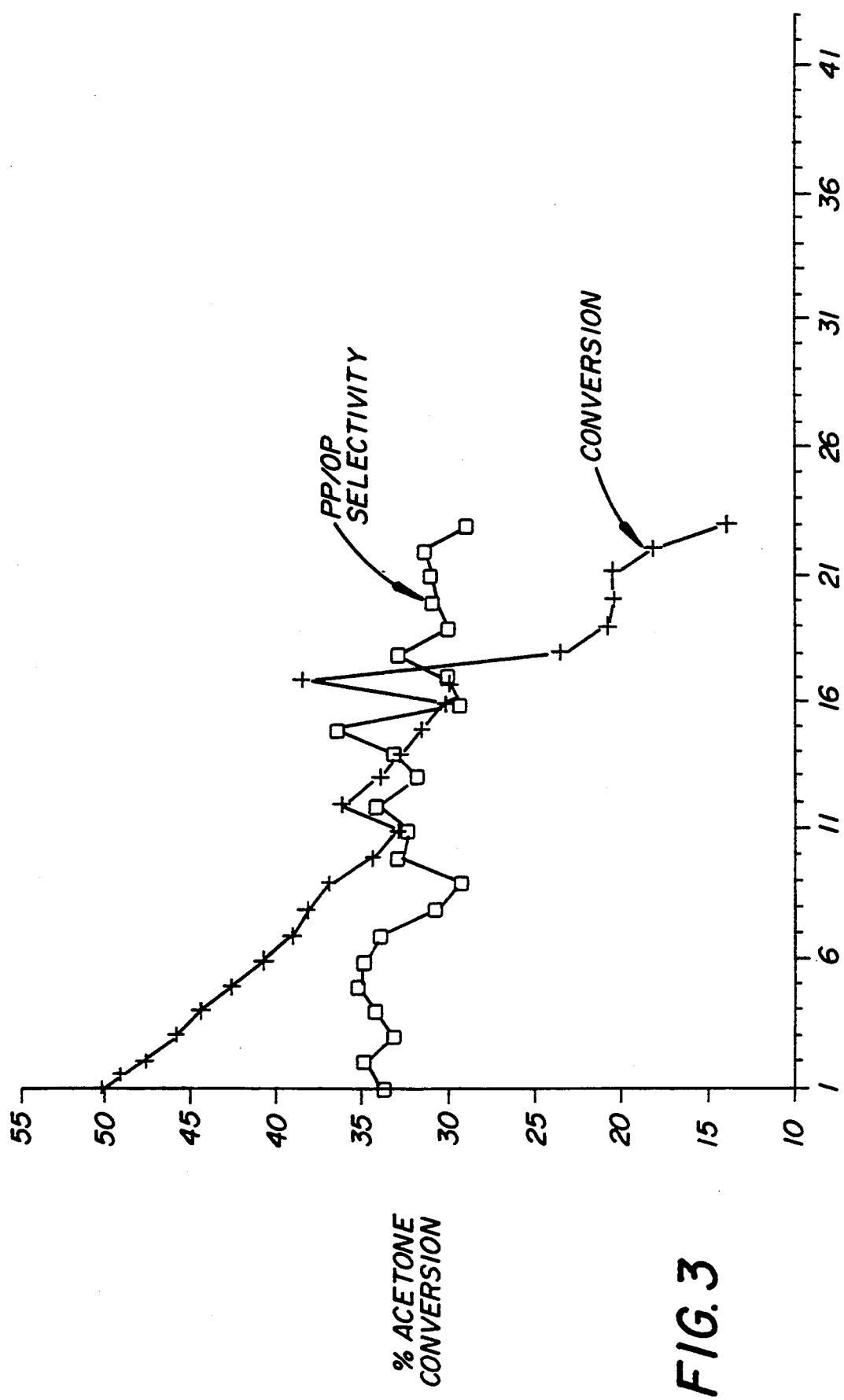
FIGS. 3 and 4 are graphical representations showing the catalyst life extension resulting from practice of the invention when the catalyst is a sulfonated polystyrene with mercaptan promotor groups ionically bound thereto.

The reactant feed used was a 5% acetone in pure phenol mixture. The reactor was run for 43 days. As shown in the accompanying drawing of FIG. 3 (symbol "+"), the catalyst began at approximately 50-55% acetone conversion and steadily deactivated.

Product selectivity was relatively constant through the period as expected, and pp/op' decayed only slightly from ~35 to ~30 (as shown by the symbol "□").

EXAMPLE 4

Figure 4:
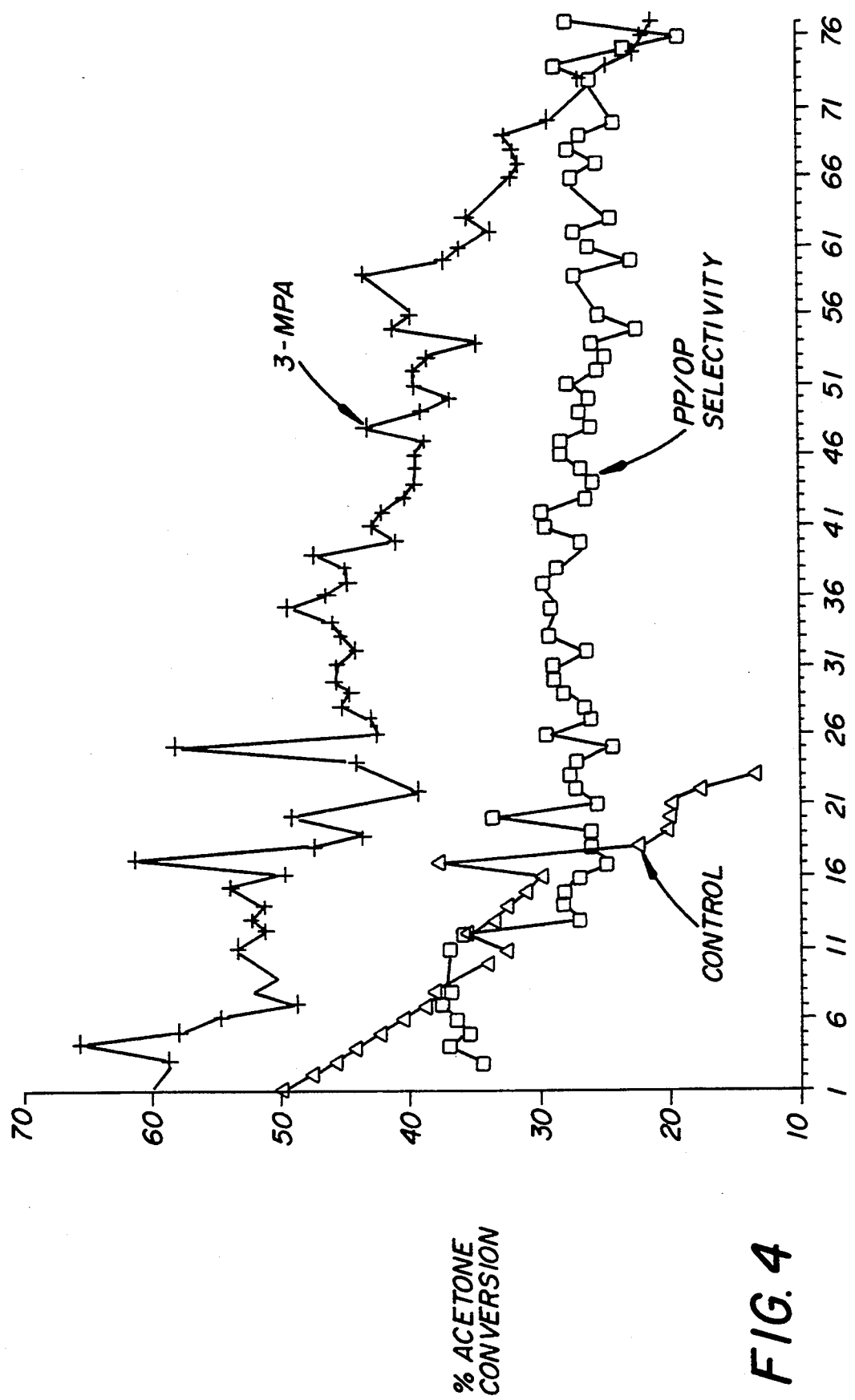

The general procedure of Example 3, supra., was repeated except that 1500 ppm of 3-mercaptanpropionic-propionic acid (~500 ppm SH groups) was added to the feed. The data obtained (symbol "+") is illustrated in FIG. 4 against a comparison of a control run made under the same conditions, but without 3-mercaptopropionic acid in the feed reaction mixture (shown with the symbol " "). Although catalyst activity decayed during the 11 week test with 3-mercaptopropionic acid in the feed, the rate of activity loss was much improved compared to the run without 3-mercaptopropionic acid.

Product sensitivity, as measured by pp/op' ratio, dropped from ~35 to 25-30 during the first 12 days but remained relatively constant for the remainder of the 77 day period (as shown by the symbol "□").

EXAMPLE 5

Repeating the procedure of Example 4, supra., but replacing the 3-mercaptopropionic acid as used therein with an equal proportion of the methyl ester thereof (methyl 3-mercaptopropionate), improvements are seen in extending the catalyst activity.

I claim:

1. In a process for the reaction of a ketone with a phenol, in the presence of an acidic cation exchange resin having organomercaptan promoter groups, the improvement which comprises; adding to the reaction mixture from about 100 to about 5000 ppm of 3-mercaptopropionic acid or the organic ester thereof.

2. The improved process of claim 1 wherein the reactants are mixed together and passed through a reaction zone in contact with the resin.

3. The improved process of claim 2 wherein the 3-mercaptopropionic acid or ester thereof is fed into the reaction zone with the mixed reactants.

4. The improved process of claim 1 wherein the ketone is acetone and the phenol is unsubstituted phenol.

5. The improved process of claim 4 carried out at a temperature within the range of from about 40° C. to 95° C.

6. The improved process of claim 1 wherein the amount of 3-mercaptopropionic acid or ester added is within the range of from about 1000 to about 4000 PPM of the reaction mixture.

7. The improved process of claim 1 wherein the resin is a sulfonated poly(styrene-divinylbenzene) copolymer having pendant groups of the formula:

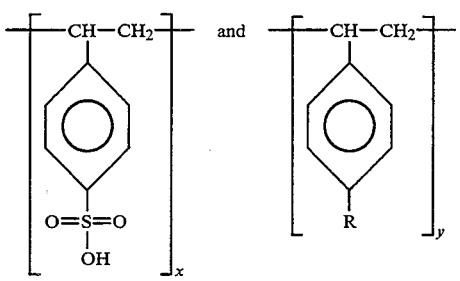

wherein x and y are integers in a ratio of from 60:40 to 99:1 (x:y); and R is a group selected from those of the formula:

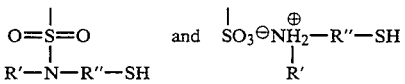

wherein R' represents hydrogen or alkyl and R" is alkylene.

8. The improved process of claim 7 wherein R is the monovalent moiety of formula:

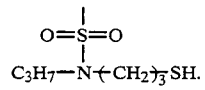

9. The improved process of claim 7 wherein R is the monovalent moiety of formula:

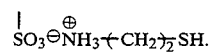

10. The improved process of claim 1 carried out continuously.

11. The improved process of claim 1 wherein the process is a batch process.

* * * * *